US008080671B2

(12) United States Patent
Guggenheim et al.

(10) Patent No.: US 8,080,671 B2
(45) Date of Patent: Dec. 20, 2011

(54) PRODUCTION OF LOW COLOR POLYETHERIMIDES

(75) Inventors: Thomas L. Guggenheim, Mt. Vernon, IN (US); Roy Ray Odle, Mt. Vernon, IN (US); Karthik Venkataraman, Evansville, IN (US)

(73) Assignee: SABIC Innovative Plastics IP B.V. (NL)

( * ) Notice: Subject to any disclaimer, the term of this patent is extended or adjusted under 35 U.S.C. 154(b) by 368 days.

(21) Appl. No.: 12/196,479

(22) Filed: Aug. 22, 2008

(65) Prior Publication Data

US 2009/0292128 A1    Nov. 26, 2009

Related U.S. Application Data

(60) Provisional application No. 61/055,704, filed on May 23, 2008.

(51) Int. Cl.
*C07D 209/48* (2006.01)
(52) U.S. Cl. ..................................... 548/473
(58) Field of Classification Search .................. 548/473
See application file for complete search history.

(56) References Cited

U.S. PATENT DOCUMENTS

| | | | |
|---|---|---|---|
| 3,803,085 A | 4/1974 | Takehoshi et al. |
| 3,833,546 A | 9/1974 | Takehoshi et al. |
| 3,838,097 A | 9/1974 | Wirth et al. |
| 3,847,867 A | 11/1974 | Heath et al. |
| 3,847,869 A | 11/1974 | Williams, III |
| 3,847,870 A | 11/1974 | Takekoshi |
| 3,850,885 A | 11/1974 | Takekoshi et al. |
| 3,850,964 A | 11/1974 | Williams, III |
| 3,852,242 A | 12/1974 | White |
| 3,855,178 A | 12/1974 | White et al. |
| 3,855,239 A | 12/1974 | Crivello |
| 3,879,428 A | 4/1975 | Heath et al. |
| 3,917,643 A | 11/1975 | Takekoshi et al. |
| 3,923,828 A | 12/1975 | Williams |
| 3,933,852 A | 1/1976 | Cook et al. |
| 3,957,862 A | 5/1976 | Heath et al. |
| 3,972,902 A | 8/1976 | Heath et al. |
| 3,991,004 A | 11/1976 | Takekoshi et al. |
| 4,005,102 A | 1/1977 | Cook et al. |
| 4,005,134 A | 1/1977 | Markezich |
| 4,017,511 A | 4/1977 | Williams, III |
| 4,020,069 A | 4/1977 | Johnson et al. |
| 4,048,190 A | 9/1977 | Johnson et al. |
| 4,054,577 A | 10/1977 | Relles et al. |
| 4,054,600 A | 10/1977 | Johnson |
| 4,116,980 A | 9/1978 | Webb |
| 4,128,574 A | 12/1978 | Markezich et al. |
| 4,202,993 A | 5/1980 | Takekoshi |
| 4,217,281 A | 8/1980 | Markezich et al. |
| 4,247,464 A | 1/1981 | Relles et al. |
| 4,257,953 A | 3/1981 | Williams, III et al. |
| 4,273,712 A | 6/1981 | Williams, III |
| 4,302,616 A | 11/1981 | Williams, III et al. |
| 4,318,857 A | 3/1982 | Webb et al. |
| 4,329,291 A | 5/1982 | Webb et al. |
| 4,329,292 A | 5/1982 | Webb |
| 4,329,496 A | 5/1982 | Webb |
| 4,340,545 A | 7/1982 | Webb et al. |
| 4,455,431 A | 6/1984 | Williams, III et al. |
| 4,471,125 A | 9/1984 | Verbicky, Jr. et al. |
| 4,492,806 A | 1/1985 | Mendiratta et al. |
| 4,513,141 A | 4/1985 | Brunelle et al. |
| 4,546,207 A | 10/1985 | Mendiratta et al. |
| 4,571,425 A | 2/1986 | Silva |
| 4,584,388 A | 4/1986 | Webb |
| 4,599,429 A | 7/1986 | Odle |
| 4,600,798 A | 7/1986 | Cella |
| 4,650,850 A | 3/1987 | Howson |
| 4,757,150 A | 7/1988 | Guggenheim et al. |
| 4,870,155 A | 9/1989 | Matzner et al. |
| 4,902,809 A | 2/1990 | Groeneweg et al. |
| 4,921,970 A | 5/1990 | Odle |
| 5,155,234 A | 10/1992 | Odle |
| 5,208,346 A | 5/1993 | Dellacoletta |
| 5,359,084 A * | 10/1994 | Dellacoletta et al. .......... 548/461 |
| 5,536,846 A | 7/1996 | Dellacoletta et al. |
| 5,719,295 A | 2/1998 | Dellacoletta et al. |
| 5,851,837 A | 12/1998 | Stokes et al. |
| 5,936,099 A | 8/1999 | Dellacoletta et al. |
| 6,008,374 A | 12/1999 | Dellacoletta et al. |
| 6,590,108 B1 | 7/2003 | Odle et al. |
| 6,710,187 B2 | 3/2004 | Guggenheim et al. |
| 6,949,622 B2 | 9/2005 | Silvi et al. |
| 7,122,619 B2 | 10/2006 | Silvi et al. |

(Continued)

FOREIGN PATENT DOCUMENTS

GB    2280183 A    1/1995

(Continued)

OTHER PUBLICATIONS

Hsiao, Sheng-Huei, et al., Synthesis and Properties of Poly(ether imide)s Derived From 4,4'-(1,5-naphthylenedioxy)Diphthalic Anhydride and Various Aromatic Diamines, *Macromol. Chem. Phys.*, 1997, pp. 2153-2162, vol. 198.

(Continued)

*Primary Examiner* — Rei-tsang Shiao
(74) *Attorney, Agent, or Firm* — Cantor Colburn LLP; Diderico van Eyl

(57) ABSTRACT

The production of low color polyetherimides, including its intermediates, such as bisimides and diaryl diether dianhydrides, may be affected by producing an improved purity intermediate of 4-nitro-N-alkylphthalimide. A salt, such as alkali metal carbonate or alkali metal hydrogen carbonate, is added to an aqueous mixture of 4-nitro-N-alkylphthalimide and 3-nitro-N-alkylphthalimide to selectively hydrolyze the imide linkage of 3-nitro-N-alkylphthalimide forming a water-soluble acid-amide salt. An organic solvent is added to this salt mixture to phase separate 4-nitro-N-alkylphthalimide having dissolved in the organic solvent from acid-amide salt of 3-nitro-N-alkylphthalimide having dissolved in water.

32 Claims, No Drawings

U.S. PATENT DOCUMENTS

| | | |
|---|---|---|
| 7,153,394 B2 | 12/2006 | Guggenheim et al. |
| 7,226,989 B2 | 6/2007 | Silvi et al. |
| 2007/0073063 A1 | 3/2007 | Stella et al. |

FOREIGN PATENT DOCUMENTS

| | | |
|---|---|---|
| JP | 63211277 A2 | 9/1988 |

OTHER PUBLICATIONS

Lee, Yeong-Beom, et al., Simple Synthetic Route to Soluble Polyimides Via Nitro-Displacement Reaction and Their Second-Order Nonlinear Optical Properties, *J. Mater. Chem.*, 1999, pp. 2345-2350, vol. 9.

Leu, C.-M,, et al,, Dendritic Poly(ether-imide)s: Synthesis, Characterization, and Modification, *Polymer*, 2001, pp. 2339-2348, vol. 42.

Leu, C.-M., et al., Synthesis and Characterization of Dendritic Poly(ether imide)s, *Macromolecules*, 2000, pp. 2855-2861, vol. 33.

Wu, Fang-Iy and Shu, Ching-Fong, Hyperbranched Aromatic Poly(ether imide)s: Synthesis, Characterization, and Modification, *Journal of Polymer Science: Part A: Polymer Chemistry*, 2001, pp. 2536-2546, vol. 39.

U.S. Appl. No. 11/755,415, filed May 30, 2007, Silvi, et al.

U.S. Appl. No. 12/059,217, filed Mar. 31, 2008, Giammattei, et al.

009121499, DE, 2009, XP abstract.

\* cited by examiner

PRODUCTION OF LOW COLOR POLYETHERIMIDES

CROSS REFERENCE TO RELATED APPLICATIONS

The present application claims the benefit of and priority to U.S. Provisional Application No. 61/055,704, filed May 23, 2008, titled "Production of Low Color Polyetherimides", which is herein incorporated by reference.

FIELD

The present invention relates generally to the production of polyetherimides and, more specifically, to the production of low color polyetherimides by producing an improved purity intermediate of 4-nitro-N-alkylphthalimide.

BACKGROUND

Polyetherimides (PEIs) are high performance polymers used in a variety of industries such as automotive, aerospace, optics and the like. There are many chemical synthesis processes for preparation of PEIs. In one such process diaryl diether dianhydride, such as bisphenol A dianhydride (BPADA), is polymerized by reaction with a diamine to form PEI. Diaryl diether dianhydride (DA) with predominately 4-ether linkages are sometimes preferred over 3-ether or 3,4-ether linkages since the resulting PEI has lower color properties. Lower color resins have a wider range of commercial uses, e.g., ophthalmic applications. Use of lower color resins also makes it easier to perform color matching applications. Many customers prefer lower color resins, because it enables them to make more transparent parts and develop a wide array of products that meet customer expectations.

Manufacturing processes to produce BPADA typically have an end product containing about 93 percent 4,4-BPADA, about 6.5 percent 3,4-BPADA, and about 0.5 percent 3,3-BPADA. The amount of 3-ether and 3,4-ether linkages is often determined by the purity of intermediates used in manufacturing BPDA. A simplified commercial route to BPADA includes the imidization of phthalic anhydride to N-alkyl phthalimide, which is nitrated to nitro-N-alkylphthalimide (NPI). Following this step is the salt displacement of NPI utilizing an alkali metal bisphenoxide salt to form a diether bisimide. Processes to form the diether bisimide by salt displacement of NPI with an alkali metal bisphenoxide are known can be found in the literature, e.g. U.S. Pat. No. 4,273,712. The diether bisimide can then be converted to a dianhydride as shown, for example, in U.S. Pat. Nos. 4,329,291, 4,329,292, 4,329,496, and 4,340,545.

It has been discovered that the nitration step to manufacture of polyetherimides as described above, produces mixtures containing 4-nitro-N-alkylphthalimide, 3-nitro-N-alkylphthalimide, and proton bearing impurities. Unfortunately, this results in polymers having undesired color properties. The presence of the 3 percent by weight of 3-NPI and 97 percent by weight 4-NPI after nitration above dictates that about 6 percent by weight of the BPADA produced contains the 3,4-isomer.

For the foregoing reasons, there is a need to develop an improved process for isolating purer 4-nitro-N-alkylphthalimide.

SUMMARY

The present invention provides for the removal of 3-nitro-N-alkylphthalimide and proton-bearing impurities when producing the desired 4-nitro-N-alkylphthalimide intermediate for use in manufacturing bisimides, diaryl diether dianhydrides and polyetherimides. Having a high purity intermediate provides for improved clarity with respect to resin products manufactured therefrom. In one embodiment of the present invention a process for isolating 4-nitro-N-alkylphthalimide from an aqueous mixture of 4-nitro-N-alkylphthalimide and 3-nitro-N-alkylphthalimide comprises the steps of:

(a) providing a first mixture comprising (i) solids comprising 4-nitro-N-alkylphthalimide and 3-nitro-N-alkylphthalimide and (ii) water;

(b) adding a salt selected from the group consisting of alkali metal carbonates, alkali metal hydrogen carbonates, alkaline earth metal carbonates, hydrogen carbonates and mixtures thereof to the first mixture, thereby forming a second mixture;

(c) stirring the second mixture under conditions sufficient for selective hydrolysis of the imide linkage of 3-nitro-N-alkylphthalimide into a water-soluble acid-amide salt of 3-nitro-N-alkylphthalimide, thereby forming a third mixture;

(d) adding an organic solvent to the third mixture, thereby forming a fourth mixture comprising (i) an organic phase comprising 4-nitro-N-alkylphthalimide dissolved in the organic solvent and (ii) an aqueous phase comprising dissolved acid-amide salt of 3-nitro-N-alkylphthalimide; and (e) separating the organic phase from the aqueous phase.

In preferred embodiment of the present invention, a process for isolating 4-nitro-N-alkylphthalimide from an aqueous mixture of 4-nitro-N-alkylphthalimide, 3-nitro-N-alkylphthalimide and proton-bearing impurities comprises the steps of:

(a) providing a first mixture comprising a water slurry comprising solids comprising 4-nitro-N-alkylphthalimide, 3-nitro-N-alkylphthalimide, and proton-bearing impurities;

(b) adding a salt selected from the group consisting of sodium carbonate and sodium hydrogen carbonate to the first mixture, thereby forming a second mixture;

(c) stirring the second mixture under conditions sufficient for selective hydrolysis of the imide linkage of 3-nitro-N-alkylphthalimide into a water-soluble acid-amide salt of 3-nitro-N-alkylphthalimide, and to convert the proton-bearing impurities to water soluble alkali metal salts, thereby forming a third mixture;

(d) adding toluene to the third mixture, thereby forming a fourth mixture comprising (i) an organic phase comprising 4-nitro-N-alkylphthalimide dissolved in toluene and (ii) an aqueous phase comprising dissolved acid-amide salt of 3-nitro-N-alkylphthalimide and alkali metal salts of proton-bearing impurities; and (e) separating the organic phase from the aqueous phase.

In another embodiment of the present invention, a process for reducing the yellowness index of a bisimide comprises the steps of:

(a) nitrating N-alkylphthalimide in an acid selected from the group consisting of nitric acid and mixtures of nitric acid and sulfuric acid;

(b) washing with water the product of step (a) to form a first mixture comprising (i) solids comprising 4-nitro-N-alkylphthalimide, 3-nitro-N-alkylphthalimide, and proton-bearing impurities and (ii) water;

(c) adding a salt selected from the group consisting of alkali metal carbonates, alkali metal hydrogen carbonates, alkaline earth metal carbonates, hydrogen carbonates and mixtures thereof to the first mixture, thereby forming a second mixture;

(d) stirring the second mixture under conditions sufficient for selective hydrolysis of the imide linkage of 3-nitro-N-alkylphthalimide into a water-soluble acid-amide salt of 3-nitro-N-alkylphthalimide and to convert the proton-bearing impurities to water soluble alkali metal salts, thereby forming a third mixture;

(e) adding an organic solvent to the third mixture, thereby forming a fourth mixture comprising (i) an organic phase comprising 4-nitro-N-alkylphthalimide dissolved in the organic solvent and (ii) an aqueous phase comprising dissolved acid-amide salt of 3-nitro-N-alkylphthalimide and alkali metal salts of the proton-bearing impurities;

(f) separating the organic phase from the aqueous phase and distilling a portion of the organic solvent from the organic phase to form an anhydrous mixture of 4-nitro-N-alkylphthalimide and the organic solvent; and (g) reacting the anhydrous mixture of 4-nitro-N-alkylphthalimide and the organic solvent with an anhydrous composition comprising alkali metal bisphenoxide salt in a second solvent in the presence of a phase transfer catalyst, thereby forming a bisimide.

In still another embodiment of the present invention, a process for reducing the yellowness index of a diaryl diether dianhydride comprises the steps of:

(a) nitrating N-alkylphthalimide in an acid selected from the group consisting of nitric acid and mixtures of nitric acid and sulfuric acid;

(b) washing with water the product of step (a) to form a first mixture comprising (i) solids comprising 4-nitro-N-alkylphthalimide, 3-nitro-N-alkylphthalimide, and proton-bearing impurities and (ii) water;

(c) adding a salt selected from the group consisting of alkali metal carbonates, alkali metal hydrogen carbonates, alkaline earth metal carbonates, hydrogen carbonates and mixtures thereof to the first mixture, thereby forming a second mixture;

(d) stirring the second mixture under conditions sufficient for selective hydrolysis of the imide linkage of 3-nitro-N-alkylphthalimide into a water-soluble acid-amide salt of 3-nitro-N-alkylphthalimide and to convert the proton-bearing impurities to water soluble alkali metal salts, thereby forming a third mixture;

(e) adding an organic solvent to the third mixture, thereby forming a fourth mixture comprising (i) an organic phase comprising 4-nitro-N-alkylphthalimide dissolved in the organic solvent and (ii) an aqueous phase comprising dissolved acid-amide salt of 3-nitro-N-alkylphthalimide and alkali metal salts of the proton-bearing impurities;

(f) separating the organic phase from the aqueous phase and distilling a portion of the organic solvent from the organic phase to form an anhydrous mixture of 4-nitro-N-alkylphthalimide and the organic solvent;

(g) reacting the anhydrous mixture of 4-nitro-N-alkylphthalimide and the organic solvent with an anhydrous composition comprising alkali metal bisphenoxide salt in a second solvent in the presence of a phase transfer catalyst, thereby forming a bisimide; and (h) reacting the bisimide of step (g) with aqueous phthalic anhydride in the presence of a second catalyst to form a diaryl diether dianhydride.

In still another embodiment of the present invention, a process for reducing the yellowness index of a polyetherimides comprises the steps of:

(a) nitrating N-alkylphthalimide in an acid selected from the group consisting of nitric acid and mixtures of nitric acid and sulfuric acid;

(b) washing with water the product of step (a) to form a first mixture comprising (i) solids comprising 4-nitro-N-alkylphthalimide and 3-nitro-N-alkylphthalimide, and proton-bearing impurities and (ii) water;

(c) adding a salt selected from the group consisting of alkali metal carbonates, alkali metal hydrogen carbonates, alkaline earth metal carbonates, hydrogen carbonates and mixtures thereof to the first mixture, thereby forming a second mixture;

(d) stirring the second mixture under conditions sufficient for selective hydrolysis of the imide linkage of 3-nitro-N-alkylphthalimide into a water-soluble acid-amide salt of 3-nitro-N-alkylphthalimide and to convert the proton-bearing impurities to water soluble alkali metal salts, thereby forming a third mixture;

(e) adding an organic solvent to the third mixture, thereby forming a fourth mixture comprising (i) an organic phase comprising 4-nitro-N-alkylphthalimide dissolved in the organic solvent and (ii) an aqueous phase comprising dissolved acid-amide salt of 3-nitro-N-alkylphthalimide and alkali metal salts of proton-bearing impurities;

(f) separating the organic phase from the aqueous phase and distilling a portion of the organic solvent from the organic phase to form an anhydrous mixture of 4-nitro-N-alkylphthalimide and the organic solvent;

(g) reacting the anhydrous mixture of 4-nitro-N-alkylphthalimide and the organic solvent with an anhydrous composition comprising alkali metal bisphenoxide salt in a second solvent in the presence of a phase transfer catalyst, thereby forming a bisimide;

(h) reacting the bisimide of step (g) with aqueous phthalic anhydride in the presence of a second catalyst to form a diaryl diether dianhydride; and (i) polymerizing the diaryl diether dianhydride of step (h) to form a polyetherimide.

Preferably, in each of the embodiments, the salt is added in an amount ranging from 0.1 to 7 weight percent of salt, based on the total weight percent of solids in the first mixture, and more preferably from 1 to 5 weight percent. The salt is preferably sodium carbonate or sodium hydrogen carbonate and added as an aqueous solution. The second mixture is preferably stirred allowing for selective hydrolysis for a period ranging from 2 hours to 48 hours, more preferably from 2 to 8 hours, and even more preferably from 2 to 4 hours. The organic solvent is preferably toluene, xylene, anisole, chlorobenzene or benzene, and more preferably toluene. Other aromatic aprotic solvents can also be employed.

The organic phase preferably comprises from more than 0 to less than 2 weight percent 3-nitro-N-alkylphthalimide and proton-bearing impurities, based on the total weight percent of 3-nitro-N-alkylphthalimide, 4-nitro-N-alkylphthalimide and proton-bearing impurities. Even more preferably, the organic phase comprises from more than 0 to less than 1 weight percent 3-nitro-N-alkylphthalimide and more than 0 to less 500 parts per million (ppm) proton-bearing impurities, based on the total weight percent of 3-nitro-N-alkylphthalimide, 4-nitro-N-alkylphthalimide and proton-bearing impurities.

DESCRIPTION

The invention is based on the unexpected discovery that by using certain carbonates under certain conditions, it is now possible to isolate 4-nitro-N-alkylphthalimide from mixtures containing 4-nitro-N-alkylphthalimide, 3-nitro-N-alkylphthalimide, and proton-bearing impurities and water. The ability to isolate 4-nitro-N-alkylphthalimide in such a manner enables 4-nitro-N-alkylphthalimide to be used as an intermediate for in manufacturing bisimides, diaryl diether dianhydrides and polyetherimides having very useful low color properties.

In this specification and in the claims, which follow, reference will be made to a number of terms which shall be defined to have the following meanings.

The singular forms "a," "an," and "the" include plural referents unless the context clearly dictates otherwise.

"Optional" or "optionally" means that the subsequently described event or circumstance may or may not occur, and that the description includes instances where the event occurs and instances where it does not.

"Combination" as used herein includes mixtures, copolymers, reaction products, blends, composites, and the like.

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed in this patent application. Because these ranges are continuous, they include every value between the minimum and maximum values. Values expressed as "greater than about" or "less than about" are inclusive the stated endpoint, e.g., "greater than about 3.5" encompasses the value of 3.5.

Although process steps are listed alphabetically, it is understood that process steps do not have to be necessarily distinct or sequential and that the invention includes embodiments in which process steps can overlap as well as embodiments in which the sequence of steps are not sequential.

The Yellowness Index (YI) of the polyetherimide or the monomers used to make the polymer can be measured in accordance with ASTM E313 or ASTM D-1925 or any functionally equivalent method Generally, the Yellowness Index is a number calculated from spectrophotometric data that describes the change in color of a test sample from clear or white toward yellow. This test is most commonly used to evaluate color changes in a material, e.g., color changes caused by real or simulated outdoor exposure or process conditions. Test sample packaging, handling, and preparation (preferably no cleaning) can affect the test results by modifying the surface of the sample. Since YI testing is often a series of comparative measurements over extended periods of time, these factors should be defined and documented prior to any testing. Suitable spectrophometers include any spectrometer that can perform ASTM E313 or ASTM D-1925, and are not limited to BYK Gardner Spectrophotometer or the Macbeth Color Eye 7000 UV/VIS Spectrophotometer. After specifying the illuminant, observer angle, and the reference color, the test sample is inserted into the specimen holder, and the spectrophotometer takes the reading. Multiple samples should be measured and the readings averaged.

Polyetherimides of the present invention can exhibit relatively lower YI values as compared to polyetherimides made from other processes. In one embodiment, the polyetherimide can have a yellowness index of from 30 to less than 65, as measured by ASTM D-1925. In another embodiment, the polyetherimide can have a yellowness index of from 50 to less than 60, as measured by ASTM D-1925. However, it is understood that regardless of which method is used to determine YI, e.g., ASTM D-1925 or ASTM-E-313, a polyetherimide made in accordance with the present invention will exhibit a yellowness index that is lower as compared to a polyetherimide made from a process that does not add a salt selected from the group consisting of alkali metal carbonates, alkali metal hydrogen carbonates, alkaline earth metal carbonates, hydrogen carbonates and mixtures thereof during the process, e.g. sodium bicarbonate.

The present invention provides a process to isolate 4-nitro-N-alkylphthalimide (4NPI) from an aqueous mixture of 4-nitro-N-alkylphthalimide, 3-nitro-N-alkylphthalimide (3NPI) and proton-bearing impurities providing a purified intermediate of 4NPI. The aqueous mixture preferably has been obtained from the nitration of N-alkylphthalimide in either nitric acid or mixtures of nitric acid and sulfuric acid and subsequent water washing to remove such acids. Various known nitration processes may be employed as desired, such as that disclosed in U.S. Pat. No. 4,902,809 to Groeneweg et al. and U.S. Pat. No. 4,921,970 to Odle, both herein incorporated by reference. The process of the present invention isolates 4NPI by reducing the amount of 3NPI and proton-bearing impurities in the aqueous mixture through the treatment of the aqueous mixture with a salt selected from the group of alkali metal carbonates, alkali metal hydrogen carbonates, alkali metal hydrogen carbonates, alkaline earth metal carbonates, hydrogen carbonates and mixtures thereof. Preferably the salt is sodium bicarbonate. The aqueous mixture containing the salt is stirred under conditions which allow for the selective hydrolysis of the imide linkage of 3NPI forming a water-soluble acid-amid salt of 3NPI. The proton-bearing impurities are converted to water soluble alkali metal salts. An organic solvent, preferably toluene, is thereafter added resulting in two phase mixture of an organic phase comprising 4NPI dissolved in the organic solvent and an aqueous phase comprising dissolved acid-amide salt of 3NPI and alkali metal salts of proton-bearing impurities. The two phases are separated by known techniques to provide a purified intermediate of 4NPI.

In one embodiment of the present invention a process for isolating 4-nitro-N-alkylphthalimide from an aqueous mixture of 4-nitro-N-alkylphthalimide and 3-nitro-N-alkylphthalimide comprises the steps of:

(a) providing a first mixture comprising (i) solids comprising 4-nitro-N-alkylphthalimide and 3-nitro-N-alkylphthalimide and (ii) water;

(b) adding a salt selected from the group consisting of alkali metal carbonates, alkali metal hydrogen carbonates, alkaline earth metal carbonates, hydrogen carbonates and mixtures thereof to the first mixture forming a second mixture;

(c) stirring the second mixture under conditions sufficient for selective hydrolysis of the imide linkage of 3-nitro-N-alkylphthalimide into a water-soluble acid-amide salt of 3-nitro-N-alkylphthalimide, thereby forming a third mixture;

(d) adding an organic solvent to the third mixture, thereby forming a fourth mixture comprising (i) an organic phase comprising 4-nitro-N-alkylphthalimide dissolved in the organic solvent and (ii) an aqueous phase comprising dissolved acid-amide salt of 3-nitro-N-alkylphthalimide; and (e) separating the organic phase from the aqueous phase.

The alkyl group within the 4-nitro-N-alkylphthalimides according to the present invention is preferably a $C_1$ to $C_{18}$ alkyl, more preferably a $C_1$ to $C_4$ alkyl. Preferably, the first mixture is elevated to a temperature ranging from 20 to 60° C. The first mixture is preferably provided comprising from 10 to 40 weight percent solids, more preferably from 20 to 30 weight percent solids, and from 90 to 60 weight percent water, more preferably from 80 to 70 weight percent water.

The first mixture may comprise proton-bearing impurities such as residual nitric acids, sulfuric acids, nitrophthalic acids, oxalic acids, and other organic acids, and combinations thereof. In this instance, in step (c), the proton-bearing impurities are converted to water soluble alkali metal salts and, in step (d), the aqueous phase also comprises dissolved alkali metal salts of the proton-bearing impurities. The solids within the first mixture may comprise from 94.0 to 99.9 weight percent 4-nitro-N-alkylphthalimide, from 0.1 to 5.0 weight percent 3-nitro-N-alkylphthalimide, and from more than 0 to 1.0 weight percent proton-bearing impurities. Preferably, the first mixture is formed by nitrating N-alkylphthalimide in an acid selected from the group consisting of nitric acid and mixtures of nitric acid and sulfuric acid to form a nitration product, and washing with water the nitration product to form the first mixture. The first mixture may further comprises a member selected from the group consisting of 4-substituted-nitro-N-alkylphthalimide, 3-substituted-nitro-N-alkylphthalimide, and mixtures thereof; wherein substituted substituents are selected from the group consisting of chloro substituents, bromo substituents, fluoro substituents, and combinations thereof.

The salt is preferably added as an aqueous solution also at a temperature ranging from 20 to 60° C. The salt is added in an amount ranging from 0.1 to 7 weight percent of salt, based on the total weight percent of solids in the first mixture. More preferably the salt is added from 1 to 5 weight percent. The stirring of the first mixture and the salt, which forms the second mixture, preferably is conducted at a temperature ranging from 20 to 60° C. The salt is preferably sodium carbonate or sodium hydrogen carbonate.

In order to sufficiently hydrolyze the imide linkages of 3NPI into a water-soluble acid-amid salt of 3NPI forming the third mixture, the second mixture is preferably stirred for a period ranging from 2 to 48 hours, more preferably 2 to 8 hours, and even more preferably from 2 to 4 hours. The third mixture preferably has a pH ranging from 8.5 to 12.

After completion of the hydrolysis of the 3NPI to the corresponding amide-acid salt, an organic solvent is added to the third mixture forming the fourth mixture. The organic solvent is selected from the group consisting of toluene, xylene, chlorobenzene, anisole and benzene, and is preferably toluene. Other aromatic aprotic solvents can also be employed. The two phase mixture is heated from 50 to 100° C. to effect dissolution of the 4NPI into the aromatic solvent. The organic phase of the fourth mixture comprises from more than 0 to less than 2 weight percent 3-nitro-N-alkylphthalimide and proton-bearing impurities, based on the total weight percent of 3-nitro-N-alkylphthalimide, 4-nitro-N-alkylphthalimide and proton-bearing impurities.

Preferably, the organic phase comprises from more than 0 to less than 1 weight percent 3-nitro-N-alkylphthalimide and more than 0 to less 500 ppm proton-bearing impurities, based on the total weight percent of 3-nitro-N-alkylphthalimide, 4-nitro-N-alkylphthalimide and proton-bearing impurities.

In one embodiment, hydrolysis and organic phase separation in the invention can occur as shown below:

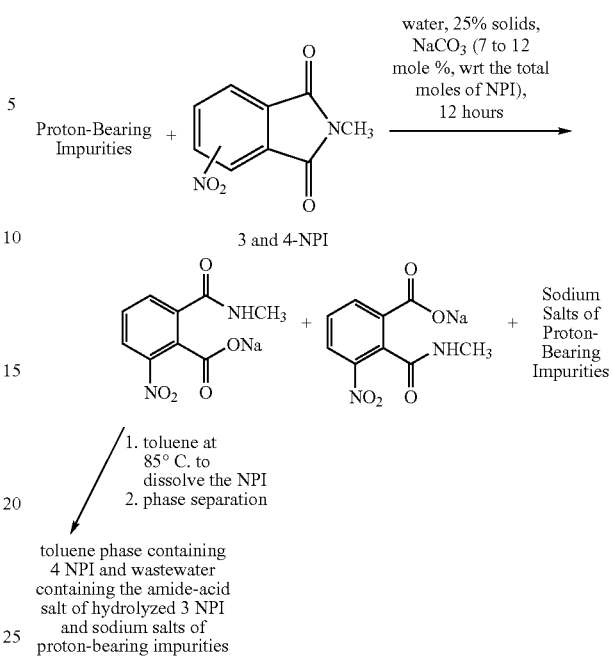

During the process of the present invention, some 4NPI is lost as the corresponding amide-acid salt. The third mixture is then contacted with toluene at 85° C., where upon the 4NPI and any remaining 3NPI dissolve in the toluene and the amide-acids and salts of proton-bearing impurities dissolve in the water. The amount of toluene used results in a 1 to 60 percent by weight solution of NPI in toluene. The phases are separated in a decanter and the 4NPI/toluene phase moves forward in the process to make products such as bisimide, diaryl diether dianhydrides or polyetherimides now enriched in the 4,4-isomer.

In a preferred embodiment of the process for isolating 4-nitro-N-alkylphthalimide from an aqueous mixture of 4-nitro-N-alkylphthalimide and 3-nitro-N-alkylphthalimide, the first mixture comprises a water slurry comprising solids comprising 4-nitro-N-alkylphthalimide, 3-nitro-N-alkylphthalimide, and proton-bearing impurities. The first mixture preferably comprises from 20 to 30 weight percent solids and from 80 to 70 weight percent water. The solids preferably comprise from 94.0 to 99.9 weight percent 4-nitro-N-alkylphthalimide, from 0.1 to 5.0 weight percent 3-nitro-N-alkylphthalimide, and from more than 0 to 1.0 weight percent proton-bearing impurities. The salt, which is added to the first mixture to form a second mixture, is sodium carbonate and/or sodium hydrogen carbonate. The salt is preferably added in an amount ranging from 1 to 5 weight percent of salt, based on the total weight percent of solids in the first mixture. The first mixture and through creation of the third mixture are preferably at a temperature ranging from 20 to 60° C. Stirring preferably occurs from a period ranging from 2 to 48 hours. After selective hydrolysis of the imide linkage of 3-nitro-N-alkylphthalimide into a water-soluble acid-amide salt of 3-nitro-N-alkylphthalimide and converting proton-bearing impurities to water soluble alkali metal salts forming a third mixture, toluene is added to the third mixture thereby forming a fourth mixture comprising (i) an organic phase comprising 4-nitro-N-alkylphthalimide dissolved in toluene and (ii) an aqueous phase comprising dissolved acid-amide salt of 3-nitro-N-alkylphthalimide and alkali metal salts of proton-bearing impurities. The organic phase is separated from the aqueous phase. The organic phase preferably comprises from more than 0 to less than 2 weight percent 3-nitro-N-alkylphthalimide and proton-bearing impurities, based on the total weight percent of 3-nitro-N-alkylphthalimide, 4-nitro-N-alkylphthalimide and proton-bearing impurities. More preferably, the organic phase comprises from more than 0 to less than 1 weight percent 3-nitro-N-alkylphthalimide and more than 0 to less 500 ppm proton-bearing impurities, based on the total weight percent of 3-nitro-N-alkylphthalimide, 4-nitro-N-alkylphthalimide and proton-bearing impurities.

In another embodiment of the present invention, a process for reducing the yellowness index of a bisimide comprises many of the same steps as set forth above. The process rather begins with first mixture having been made by nitrating N-alkylphthalimide in an acid selected from the group consisting of nitric acid and mixtures of nitric acid and sulfuric acid and the separated organic phase is reacted with an aqueous solution of alkali metal bisphenoxide salt thereby forming a bisimide. The steps for this process are comprised of:

(a) nitrating N-alkylphthalimide in an acid selected from the group consisting of nitric acid and mixtures of nitric acid and sulfuric acid;
(b) washing with water the product of step (a) to form a first mixture comprising (i) solids comprising 4-nitro-N-alkylphthalimide, 3-nitro-N-alkylphthalimide and proton-bearing impurities and (ii) water;
(c) adding a salt selected from the group consisting of alkali metal carbonates, alkali metal hydrogen carbonates, alkaline earth metal carbonates, hydrogen carbonates and mixtures thereof to the first mixture, thereby forming a second mixture;
(d) stirring the second mixture under conditions sufficient for selective hydrolysis of the imide linkage of 3-nitro-N-alkylphthalimide into a water-soluble acid-amide salt of 3-nitro-N-alkylphthalimide and to convert the proton-bearing impurities to water soluble alkali metal salts, thereby forming a third mixture;
(e) adding an organic solvent to the third mixture, thereby forming a fourth mixture comprising (i) an organic phase comprising 4-nitro-N-alkylphthalimide dissolved in the organic solvent and (ii) an aqueous phase comprising dissolved acid-amide salt of 3-nitro-N-alkylphthalimide and alkali metal salts of proton-bearing impurities;
(f) separating the organic phase from the aqueous phase and distilling a portion of the organic solvent from the organic phase to form an anhydrous mixture of 4-nitro-N-alkylphthalimide and the organic solvent; and
(g) reacting the anhydrous mixture of 4-nitro-N-alkylphthalimide and the organic solvent with an anhydrous composition comprising alkali metal bisphenoxide salt in a second solvent in the presence of a phase transfer catalyst, thereby forming a bisimide.

The alkyl group within the 4-nitro-N-alkylphthalimides according to the present invention is preferably a $C_1$ to $C_{18}$ alkyl, more preferably a $C_1$ to $C_4$ alkyl, and even more preferably 4-nitro-N-methylphthalimide. Preferably, the first mixture is elevated to a temperature ranging from 20 to 60° C. The first mixture is preferably provided comprising from 10 to 40 weight percent solids, more preferably from 20 to 30 weight percent solids, and from 90 to 60 weight percent water, more preferably from 80 to 70 weight percent water.

The proton-bearing impurities may be residual nitric acids, sulfuric acids, nitrophthalic acids, oxalic acids, other organic acids, and combinations thereof. The solids within the first mixture may comprise from 94.0 to 99.9 weight percent 4-nitro-N-alkylphthalimide, from 0.1 to 5.0 weight percent 3-nitro-N-alkylphthalimide, and from more than 0 to 1.0 weight percent proton-bearing impurities.

The salt is preferably added as an aqueous solution also at a temperature ranging from 20 to 60° C. The salt is added in an amount ranging from 0.1 to 7 weight percent of salt, based on the total weight percent of solids in the first mixture. More preferably the salt is added from 1 to 5 weight percent. The stirring of the first mixture and the salt, which forms the second mixture, preferably is conducted at a temperature ranging from 20 to 60° C. The salt is preferably sodium carbonate or sodium hydrogen carbonate.

In order to sufficiently hydrolyze the imide linkages of 3NPI into a water-soluble acid-amid salt of 3NPI forming the third mixture, the second mixture is preferably stirred for a period ranging from 2 to 48 hours, more preferably 2 to 8 hours, and even more preferably from 2 to 4 hours. The third mixture preferably has a pH ranging from 8.5 to 12.

After completion of the hydrolysis, an organic solvent is added to the third mixture forming the fourth mixture. The organic solvent is selected from the group consisting of toluene, xylene, chlorobenzene, anisole, benzene, and combinations thereof. The organic solvent is preferably toluene. Other aromatic aprotic solvents can also be employed. The two phase mixture is heated from 50 to 100° C. to effect dissolution of the 4NPI into the aromatic solvent. The organic phase of the fourth mixture comprises from more than 0 to less than 2 weight percent 3-nitro-N-alkylphthalimide and proton-bearing impurities, based on the total weight percent of 3-nitro-N-alkylphthalimide, 4-nitro-N-alkylphthalimide and proton-bearing impurities.

Preferably, the organic phase comprises from more than 0 to less than 1 weight percent 3-nitro-N-alkylphthalimide and more than 0 to less 500 ppm proton-bearing impurities, based on the total weight percent of 3-nitro-N-alkylphthalimide, 4-nitro-N-alkylphthalimide and proton-bearing impurities.

The alkali metal bisphenoxide salt that is reacted with 4-nitro-N-alkylphthalimide in the separated organic phase in step (g) to form the bisimide is preferably an alkali metal bisphenoxide salt of the formula R1—(OM)2, wherein R1 is a $C_{(6-30)}$ aromatic organic radical and M is an alkali metal ion, as more fully set forth in U.S. Pat. No. 5,536,846 and herein fully incorporated by reference. Exemplary alkali metal bisphenoxide salts include sodium and potassium salts of dihydric phenols, such as 2,2-bis-(2-hydroxyphenyl)propane, 2,4'-dihydroxyphenylmethane, bis(2-hydroxyphenyl)methane, 2,2-bis-(4-hydroxyphenyl)propane hereinafter identified as "bisphenol-A" or "BPA", 1,1-bis-(4-hydroxyphenyl)ethane, 1,1-bis-(4-hydroxyphenyl)propane, 2,2-bis-(4-hydroxyphenyl)pentane, 3,3-bis-(4-hydroxyphenyl)pentane, 4,4'-dihydroxybiphenyl, 4,4'-dihydroxy-3,3,5,5'-tetramethylbiphenyl, 2,4'-dihydroxybenzophenone, 4,4'-dihydroxydiphenylsulfone, 2,4'-dihydroxydiphenylsulfone, 4,4'-dihydroxydiphenylsulfoxide, 4,4'-dihydroxydiphenylsulfide, hydroquinone, resorcinol, 3,4'-dihydroxydiphenylmethane, 4,4'-dihydroxybenzophenone, and 4,4'-dihydroxydiphenylether. The reaction of the alkali metal bisphenoxide salt and 4-nitro-N-alkylphthalimide may be carried out in the presence of the second solvent, preferably a nonpolar organic solvent, and an effective amount of a phase transfer catalyst well known in the art. Preferably, the organic solvent and solvent are both toluene.

The bisimide can be synthesized by any suitable method. In one embodiment, for instance, the bisimide is synthesized by preparing bisphenate bis-alkali metal salt and subsequently reacting the salt with 4NPI in the presence of a phase transfer catalyst, thereby forming the bisimide. The bisphenate bis-alkali metal salt, in turn, can be prepared by numerous methods. In one embodiment, a heterogeneous mixture of an aqueous solution of alkali metal bisphenoxide salt and a nonpolar organic solvent having a boiling point of from 80 to 200° C. at 760 torr is brought to a reflux, with the removal of solvent until the alkali metal bisphenoxide salt is recovered substantially free of water. An effective amount of phase transfer catalyst also is employed. Other methods for preparing the alkali metal hydroxide salt are described in U.S. Pat. Nos. 4,202,993, 4,257,953, 4,302,616.

The phase transfer catalysts suitable for preparing the bisimide are, for example, tetrabutylammonium bromide, tetrapropylammonium bromide, tetrabutylammonium chloride, tetrabutylammonium fluoride, tetrabutylammonium acetate, tetrahexylammonium chloride, tetraheptylammonium chloride, Aliquat 336 phase transfer catalyst (methyltrioctylammonium chloride, manufactured by the General Mills Company), tetrabutylphosphonium bromide, tetraphenylphosphonium chloride, hexabutylguanidium bromide, hexabutylguanidium chloride, hexaethylguanidium bromide, and hexaethylguanidium chloride. The phase transfer catalyst can be utilized at from 0.0005 molar equivalents to 2 molar equivalents of the catalyst, per molar equivalent of alkali metal bisphenoxide salt and preferably from 0.005 to 0.05 equivalents. Nonpolar organic solvents which can be employed in the practice of the present invention include, for example, toluene, xylene, chlorobenzene, anisole, and benzene.

In another embodiment, the bisimide can be made by mixing an equivalent of a bisphenol with two equivalents of sodium hydroxide in a dipolar aprotic organic solvent, and removing water by distillation of a portion of the solvent to provide an anhydrous mixture of the disodium salt of the bisphenol; and then adding 4NPI to the anhydrous mixture of the disodium salt of the bisphenol, thereby making the bisimide under appropriate temperature and conditions.

Reaction between 4-nitro-N-alkylphthalimide and alkali metal bisphenoxide salt to produce the bisimide can be effected under an inert gas atmosphere such as nitrogen at 5 to 180° C. under substantially anhydrous conditions and in the presence of dipolar aprotic organic solvent such as dimethyl sulfoxide, N,N-dimethylformamide, N-methylpyrrolidine, N,N-dimethylacetamide, etc. Mixtures of such solvents with non-polar solvents such as toluene, chlorobenzene, etc. also can be employed. Reaction time can vary between 1 to 100 minutes or more depending upon temperature, degree of agitation, etc. A proportion of from 1.8 to 2.5 moles of 4-nitro-N-alkylphthalimide, per mole of alkali metal bisphenoxide salt may be used. While higher or lower amounts of the reactant will not substantially interfere with the formation of the desired bisimide, 2 moles of the 4-nitro-N-alkylphthalimide per mole of the alkali metal bisphenoxide salt preferably is used in preparing the bisimide. Examples of such processes can be found in the literature, U.S. Pat. Nos. 3,957,862 and 3,879,428, the contents of both incorporated herein by reference.

The bisimide can be recovered from the reaction mixture and purified by a variety of procedures. One procedure includes dissolution of the bisimide with an organic solvent such as toluene and then washing or extracting with alkali solution containing 1 to 5 percent by weight alkali, to remove by-products, e.g., monoimides, etc., and unreacted starting materials, as in U.S. Pat. No. 5,359,084

In still another embodiment of the present invention, a process for reducing the yellowness index of a diaryl diether dianhydride comprises the steps of:

(a) nitrating N-alkylphthalimide in an acid selected from the group consisting of nitric acid and mixtures of nitric acid and sulfuric acid;
(b) washing with water the product of step (a) to form a first mixture comprising (i) solids comprising 4-nitro-N-alkylphthalimide, 3-nitro-N-alkylphthalimide and proton-bearing impurities and (ii) water;
(c) adding a salt selected from the group consisting of alkali metal carbonates, alkali metal hydrogen carbonates, alkaline earth metal carbonates, hydrogen carbonates and mixtures thereof to the first mixture, thereby forming a second mixture;
(d) stirring the second mixture under conditions sufficient for selective hydrolysis of the imide linkage of 3-nitro-N-alkylphthalimide into a water-soluble acid-amide salt of 3-nitro-N-alkylphthalimide and to convert the proton-bearing impurities to water soluble alkali metal salts, thereby forming a third mixture;
(e) adding an organic solvent to the third mixture, thereby forming a fourth mixture comprising (i) an organic phase comprising 4-nitro-N-alkylphthalimide dissolved in the organic solvent and (ii) an aqueous phase comprising dissolved acid-amide salt of 3-nitro-N-alkylphthalimide and alkali metal salts of proton-bearing impurities;
(f) separating the organic phase from the aqueous phase and distilling a portion of the organic solvent from the organic phase to form an anhydrous mixture of 4-nitro-N-alkylphthalimide and the organic solvent;
(g) reacting the anhydrous mixture of 4-nitro-N-alkylphthalimide and solvent with an anhydrous composition comprising alkali metal bisphenoxide salt in a second solvent in the presence of a phase transfer catalyst, thereby forming a bisimide; and
(h) reacting the bisimide of step (g) with aqueous phthalic anhydride in the presence of a second catalyst to form a diaryl diether dianhydride.

This embodiment of the present invention adds additional step (h) over the former embodiment which forms bisimide with reduced yellowness. Thus, having a bisimide with reduced yellowness allows for the production of diaryl diether dianhydride with reduced yellowness. The second catalyst used in step (h) is preferably triethylamine. In step (e) the organic solvent is preferably toluene. In step (g), the second solvent is preferably toluene.

The bisimide resulting from step (g) can be further processed for introduction to an exchange reaction to form the diaryl diether dianhydride by removing solvent, if any, to give molten bisimide. Solvent is removed using conventional processes such as flashing off the solvent and holding the bisimide melt at approximately 260° C. This flashing step, however, need not be employed if a solventless displacement reaction is conducted using alkyls according to this invention when 4-nitro-N-butylphthalimide or a higher N-alkyl derivative is used to make the bisimide.

The exchange reaction can be conducted utilizing conventional techniques. Transformation of the bisimide preferably is carried out under known conditions by reacting the bisimide in its molten state with aqueous phthalic anhydride and triethylamine as described in U.S. Pat. No. 4,318,857 to Webb et al., the contents of which are incorporated herein by reference. It is preferable to run this reaction at a temperature in the range of 150 to 240° C. The resulting reaction product then is extracted with an organic solvent. The aqueous mixture then is stripped from the extraction solution to recover the diaryl diether dianhydride.

Other exchange techniques are described in U.S. Pat. Nos. 3,957,862 and 3,879,428, both incorporated herein by reference. For example, the bisimide is hydrolyzed with base to a tetra-acid salt, which is thereafter acidified to the tetra-acid. The tetra-acid then is dehydrated to the corresponding diaryl diether dianhydride. Hydrolysis of the bisimide to the tetra-acid salt can be affected under reflux conditions in the presence of a base such as an alkali hydroxide, including sodium hydroxide. Reaction time can vary from 1 to 24 hours or more depending upon reactants, degree of agitation, temperature, pressure, etc. The organic amine by-product can be removed by standard procedures, such as steam distillation, decantation, etc. In addiction, the rate of hydrolysis is greatly accelerated by carrying out the reaction at above atmospheric pressures at temperatures in the range of from 100 to 220° C. The tetra-acid salt thereafter can be acid/fled with a mineral acid, such as a dilute aqueous solution of hydrochloric acid, etc. The resulting tetra-acid is dehydrated and recrystallized by standard techniques, e.g., refluxing with a dehydrating agent such as acetic anhydride.

Finally, in still another embodiment of the present invention, the invention includes the step of polymerizing diaryl diether dianhydride to form polyetherimide. Preferably, the polymerization is by reacting the diaryl diether dianhydride with diamine. In view of the use of a relatively purer 4-nitro-N-alkylphthalimide, such a process provides a method for reducing the yellowness index of a polyetherimide.

More specifically, this embodiment provides a process for reducing the yellowness index of polyetherimide comprising the steps of:

(a) nitrating N-alkylphthalimide in an acid selected from the group consisting of nitric acid and mixtures of nitric acid and sulfuric acid;

(b) washing with water the product of step (a) to form a first mixture comprising (i) solids comprising 4-nitro-N-alkylphthalimide, 3-nitro-N-alkylphthalimide and proton-bearing impurities and (ii) water;

(c) adding a salt selected from the group consisting of alkali metal carbonates, alkali metal hydrogen carbonates, alkaline earth metal carbonates, hydrogen carbonates and mixtures thereof to the first mixture, thereby forming a second mixture;

(d) stirring the second mixture under conditions sufficient for selective hydrolysis of the imide linkage of 3-nitro-N-alkylphthalimide into a water-soluble acid-amide salt of 3-nitro-N-alkylphthalimide and to convert the proton-bearing impurities to water soluble alkali metal salts, thereby forming a third mixture;

(e) adding an organic solvent to the third mixture, thereby forming a fourth mixture comprising (i) an organic phase comprising 4-nitro-N-alkylphthalimide dissolved in the organic solvent and (ii) an aqueous phase comprising dissolved acid-amide salt of 3-nitro-N-alkylphthalimide and alkali metal salts of proton-bearing impurities;

(f) separating the organic phase from the aqueous phase and distilling a portion of the organic solvent from the organic phase to form an anhydrous mixture of 4-nitro-N-alkylphthalimide and the organic solvent;

(g) reacting the anhydrous mixture of 4-nitro-N-alkylphthalimide and the organic solvent with an anhydrous composition comprising alkali metal bisphenoxide salt in a second solvent in the presence of a phase transfer catalyst, thereby forming a bisimide;

(h) reacting the bisimide of step (g) with aqueous phthalic anhydride in the presence of a second catalyst to form diaryl diether dianhydride; and (i) polymerizing the diaryl diether dianhydride of step (h) to form polyetherimide.

In step (e), the organic solvent is preferably toluene. In step (g), the second solvent is preferably toluene. In step (h), the second catalyst is preferably triethylamine. In step (i), the polymerization is by reacting the diaryl diether dianhydride of step (h) with diamine. In step (i), the polyetherimide can have a yellowness index of from 50 to less than 60.

Advantageously, the present invention now provides an effective way for isolating 4-nitro-N-alkylphthalimide from an aqueous mixture of 4-nitro-N-alkylphthalimide and 3-nitro-N-alkylphthalimide, such that it is now possible to make polyetherimides of relatively low color. This method is more effective and efficient than extensive water washing of the product of nitration as is ordinarily done. While extensive water washing of the product cake is known to remove proton-bearing impurities and 3NPI, such also removes an unacceptable amount of 4-NPI. Further, water washing of the product cake often causes fouling of process equipment that handles the resulting wash water.

The present invention also provides advantages over recrystallizing 4NPI from a solvent, as described in U.S. Pat. No. 3,923,828, which requires considerable and costly plant equipment to recycle the solvent used for recrystallization and isolation of the purified product.

The invention is further described in the following illustrative examples in which all parts and percentages are by weight unless otherwise indicated.

EXAMPLES

Example 1

The purpose of this experiment was to show how the process could be carried out over a period of approximately eight hours with 3 wt % sodium bicarbonate with marginal stirring. A 1.5-liter water-jacketed vessel was charged with NPI slurry in water, containing of 24.5 wt % solids, 0.1 wt % proton-bearing impurities, and the rest water. The solids included 3.54 wt % 3-nitro-N-methylphthalimide, and the rest 4-nitro-N-methylphthalimide. The contents of the vessel were maintained at 31° C. throughout the experiment.

Sodium bicarbonate (3.0 wt % with respect to total NPI in the slurry) was dissolved in water and added to the slurry in the vessel to form a second mixture. The second mixture was comprised of 22.0 wt % NPI in water. The second mixture was stirred at 68 rpm and 31° C. to form a third mixture. A 20 gm sample of the third mixture was removed from the jacketed vessel after 8 hrs, and transferred to a 100-ml round bottom flask. Reagent grade toluene (40 mL) was then added to the third mixture in the round bottom flask to form the fourth mixture, which was stirred for 1 hr at 85° C., where upon the NPI dissolved into the toluene phase. The stirring was stopped and the phases allowed to separate. The organic phase comprised of 1.78 wt % 3-nitro-N-methylphthalimide (with respect to the weight of all nitro-N-alkylphthalimides) after the separation.

A summary of this experiment is shown in Table 1 (NM means not measured).

TABLE 1

| | Example# 1 |
|---|---|
| Stirring rate (rpm) | 68 |
| Temperature during experiment (° C.) | 31 |

TABLE 1-continued

| | Example# 1 |
|---|---|
| sodium bicarbonate w.r.t wt NPI in starting NPI slurry (wt %) | 3.0 |
| % NPI in slurry (wt %) | 24.50 |
| acid in slurry (wt %) | 0.10 |
| 3NPI in slurry, w.r.t to solids (wt %) | 3.54 |
| NPI in slurry for experiment (wt %) | 22.5 |
| 3NPI in toluene, w.r.t to total 4NPI/3NPI, after 4 h stirring with bicarbonate (wt %) | NM |
| 3NPI in toluene, w.r.t to total 4NPI/3NPI, after 8 h stirring with bicarbonate (wt %) | 2.47 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | 1.61 |

The results show that the marginal stirring rate (68 rpm), and temperature (31° C.) and 24 hour contact time of 3 wt % bicarbonate with the NPI water slurry did not result in <1% 3NPI in the 4NPI that dissolved in the toluene phase.

Example 2

The experiment in Example 1 was repeated exactly, except that the NPI slurry was contacted with bicarbonate at 41° C. instead of 31° C., and at 500 rpm stirring rate instead of 68 rpm. The results are shown in Table 2.

TABLE 2

| | Example# 2 |
|---|---|
| Stirring rate (rpm) | 500 |
| Temperature during experiment (° C.) | 41 |
| sodium bicarbonate w.r.t wt NPI in starting NPI slurry (wt %) | 3.0 |
| % NPI in slurry (wt %) | 24.50 |
| acid in slurry (wt %) | 0.10 |
| 3NPI in slurry, w.r.t to solids (wt %) | 3.54 |
| NPI in slurry for experiment (wt %) | 22.0 |
| 3NPI in toluene, w.r.t to total 4NPI/3NPI, after 4 h stirring with bicarbonate (wt %) | NM |
| 3NPI in toluene, w.r.t to total 4NPI/3NPI, after 8 h stirring with bicarbonate (wt %) | 0.35 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | 0.32 |

1. NM means not measured.

The results show that the good stirring rate (500 rpm), and higher temperature (41° C.) and 24 hour contact time of bicarbonate with the NPI water slurry did result in <1% 3NPI in the 4NPI that dissolved in the toluene phase. It was also shown that these reaction conditions resulted in the desired level of 3NPI in the toluene phase after 8 hours of contact time.

Example 3

The purpose of the Experiment was to further probe how the process could be carried out over a period of approximately 24 hours and evaluate the effect of stirring time, temperature (31° C.) and stirring rate (500 rpm). The experimental details and mixture compositions for this experiment were the same as Example 1, except that the water slurry of NPI was contacted with bicarbonate at a stirring rate of 500 rpm. A 20 gm sample of the 4NPI water slurry containing the bicarbonate was removed from the jacketed vessel after 24 hrs, and transferred to a 100-ml round bottom flask. Reagent grade toluene (40 mL) was then added to the round bottom flask to form the fourth mixture, which was stirred for 1 hr at 85° C., where upon the NPI dissolved into the toluene phase. The stirring was stopped and the phases allowed to separate. The organic phase comprised of 0.59 wt % 3-nitro-N-methylphthalimide (with respect to the weight of all nitro-N-methylphthalimides) after the separation.

A summary of this experiment is shown in Table 3 (NM means not measured).

TABLE 3

| | Example# 3 |
|---|---|
| Stirring rate (rpm) | 500 |
| Temperature during experiment (° C.) | 31 |
| sodium bicarbonate w.r.t wt NPI in starting NPI slurry (wt %) | 3.0 |
| % NPI in slurry (wt %) | 24.50 |
| acid in slurry (wt %) | 0.10 |
| 3NPI in slurry, w.r.t to solids (wt %) | 3.54 |
| NPI in slurry for experiment (wt %) | 22.0 |
| 3NPI in toluene, w.r.t to total 4NPI/3NPI, after 4 h stirring with bicarbonate (wt %) | NM |
| 3NPI in toluene, w.r.t to total 4NPI/3NPI, after 8 h stirring with bicarbonate (wt %) | 1.78 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | 0.59 |

The results show that a high stirring rate (500 rpm), at 31° C. with a 24 hour contact time of bicarbonate with the NPI water slurry did result in <1% 3NPI in the 4NPI that dissolved in the toluene phase. However, there was 1.78 wt % 3NPI in the 4NPI after 8 hours of contact time of the NPI water slurry with bicarbonate.

Example 4

The purpose of this experiment was to show the efficiency of 3NPI removal from 4NPI at marginal mixing rate (68 rpm) at 41° C. in the process. The experiment was run exactly as in Example 1 except the NPI water slurry was contacted with bicarbonate at 41° C. at 68 rpm. A sample of the bicarbonate treated slurry was contacted with toluene as in Example 1 and it was shown that 0.34 wt % of 3NPI remained in the 4NPI after 24 hours of contact time. The results are shown in Table 4.

TABLE 4

| | Example# 4 |
|---|---|
| Stirring rate (rpm) | 68 |
| Temperature during experiment (° C.) | 41 |
| sodium bicarbonate w.r.t wt NPI in starting NPI slurry (wt %) | 3.0 |
| % NPI in slurry (wt %) | 24.50 |
| acid in slurry (wt %) | 0.10 |
| 3NPI in slurry, w.r.t to solids (wt %) | 3.54 |
| NPI in slurry for experiment (wt %) | 22.0 |
| 3NPI in toluene, w.r.t to total 4NPI/3NPI, after 4 h stirring with bicarbonate (wt %) | 2.26 |
| 3NPI in toluene, w.r.t to total 4NPI/3NPI, after 8 h stirring with bicarbonate (wt %) | 1.80 |
| 3NPI in toluene, w.r.t to total 4NPI/3NPI, after 12 h stirring with bicarbonate (wt %) | 1.27 |
| 3NPI in toluene, w.r.t to total 4NPI/3NPI, after 24 h stirring with bicarbonate (wt %) | 0.34 |

Example 5

The purpose of this experiment was to show the efficiency of 3NPI removal from 4NPI at marginal mixing rate at higher temperature in the process. The experiment was run exactly as in Example 1 except the NPI water slurry was contacted with bicarbonate at 50° C. at 68 rpm. A sample of the bicarbonate treated slurry was contacted with toluene as in Example 1 and it was shown that 0.44 wt % of 3NPI remained in the 4NPI after 24 hours of contact time, and 0.57 wt % after 8 hours of contact time. Shorter contact time has beneficial economic implications. The results are shown in Table 5.

TABLE 5

|  | Example# 5 |
| --- | --- |
| Stirring rate (rpm) | 68 |
| Temperature during experiment (° C.) | 50 |
| sodium bicarbonate w.r.t wt NPI in starting NPI slurry (wt %) | 3.0 |
| % NPI in slurry (wt %) | 24.50 |
| acid in slurry (wt %) | 0.10 |
| 3NPI in slurry, w.r.t to solids (wt %) | 3.54 |
| NPI in slurry for experiment (wt %) | 22.0 |
| 3NPI in toluene, w.r.t to total 4NPI/3NPI, after 4 h stirring with bicarbonate (wt %) | NM |
| 3NPI in toluene, w.r.t to total 4NPI/3NPI, after 8 h stirring with bicarbonate (wt %) | 0.57 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | 0.44 |

Example 6

The purpose of this experiment was to show the efficiency of 3NPI removal from 4NPI at better mixing rate at higher temperature in the process. The experiment was run exactly as in Example 1 except the NPI water slurry was contacted with bicarbonate at 50° C. at 110 rpm. A sample of the bicarbonate treated slurry was contacted with toluene as in Example 1 and it was shown that 0.31 wt % of 3NPI remained in the 4NPI after 24 hours of contact time, and 0.85 wt % after 8 hours of contact time. Slightly better mixing did not result in better removal of 3NPI after 8 hours of contact time. The results are shown in Table 6.

TABLE 6

|  | Example# 6 |
| --- | --- |
| Stirring rate (rpm) | 110 |
| Temperature during experiment (° C.) | 50 |
| sodium bicarbonate w.r.t wt NPI in starting NPI slurry (wt %) | 3.0 |
| % NPI in slurry (wt %) | 24.50 |
| acid in slurry (wt %) | 0.10 |
| 3NPI in slurry, w.r.t to solids (wt %) | 3.54 |
| NPI in slurry for experiment (wt %) | 22.0 |
| 3NPI in toluene, w.r.t to total 4NPI/3NPI, after 4 h stirring with bicarbonate (wt %) | NM |
| 3NPI in toluene, w.r.t to total 4NPI/3NPI, after 8 h stirring with bicarbonate (wt %) | 0.85 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | 0.31 |

Example 7

The purpose of this experiment was to show the efficiency of 3NPI removal from 4NPI at a marginal mixing rate at higher temperature in the process. Additionally, less acidic impurities were in the starting NPI water slurry (0.07 wt % as opposed to 0.1 wt %). The experiment was run exactly as in Example 1 except the NPI water slurry was contacted with bicarbonate at 60° C. at 68 rpm. A sample of the bicarbonate treated slurry was contacted with toluene as in Example 1 and it was shown that 0.58 wt % of 3NPI remained in the 4NPI after 4 hours of contact time, and 0.49 wt % after 8 hours of contact time. Higher temperature resulted in more rapid removal of the 3NPI from the 4NPI. The results are shown in Table 7.

TABLE 7

|  | Example# 7 |
| --- | --- |
| Stirring rate (rpm) | 68 |
| Temperature during experiment (° C.) | 60 |
| sodium bicarbonate w.r.t wt NPI in starting NPI slurry (wt %) | 3.0 |
| % NPI in slurry (wt %) | 27.04 |
| acid in slurry (wt %) | 0.07 |
| 3NPI in slurry, w.r.t to solids (wt %) | 3.66 |
| NPI in slurry for experiment (wt %) | 22.0 |
| 3NPI in toluene, w.r.t to total 4NPI/3NPI, after 4 h stirring with bicarbonate (wt %) | 0.58 |
| 3NPI in toluene, w.r.t to total 4NPI/3NPI, after 8 h stirring with bicarbonate (wt %) | 0.49 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | NM |

Example 8

The purpose of this experiment was to show the efficiency of 3NPI removal from 4NPI at marginal mixing rate at a low temperature in the process. The experiment was run exactly as in Example 1 except the NPI water slurry was contacted with bicarbonate at 20° C. at 68 rpm. A sample of the bicarbonate treated slurry was contacted with toluene as in Example 1 and it was shown that 3.02 wt % of 3NPI remained in the 4NPI after 8 hours of contact time. Low temperature of mixing the NPI water slurry with bicarbonate is inadequate to remove 3NPI from the 4NPI. The results are shown in Table 8.

TABLE 8

|  | Example# 8 |
| --- | --- |
| Stirring rate (rpm) | 68 |
| Temperature during experiment (° C.) | 20 |
| sodium bicarbonate w.r.t wt NPI in starting NPI slurry (wt %) | 3.0 |
| % NPI in slurry (wt %) | 27.04 |
| acid in slurry (wt %) | 0.07 |
| 3NPI in slurry, w.r.t to solids (wt %) | 3.66 |
| NPI in slurry for experiment (wt %) | 22.0 |
| 3NPI in toluene, w.r.t to total 4NPI/3NPI, after 4 h stirring with bicarbonate (wt %) | 3.07 |
| 3NPI in toluene, w.r.t to total 4NPI/3NPI, after 8 h stirring with bicarbonate (wt %) | 3.02 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | NM |

Example 9

The purpose of this experiment was to show the efficiency of 3NPI removal from 4NPI at marginal mixing rate at higher temperature, with less sodium bicarbonate in the process. The experiment was run exactly as in Example 1 except the NPI water slurry was contacted with 1.8 wt % bicarbonate instead of 3.0 wt %, at 55° C. at 68 rpm. A sample of the bicarbonate treated slurry was contacted with toluene as in Example 1 and it was shown that 1.56 wt % of 3NPI remained in the 4NPI after 8 hours of contact time. Less bicarbonate resulted in much less 3NPI removal at 8 hours than in Examples 2, 5, and 7. The results are shown in Table 9.

TABLE 9

|  | Example# 9 |
|---|---|
| Stirring rate (rpm) | 68 |
| Temperature during experiment (° C.) | 55 |
| sodium bicarbonate w.r.t wt NPI in starting NPI slurry (wt %) | 1.8 |
| % NPI in slurry (wt %) | 27.00 |
| acid in slurry (wt %) | 0.07 |
| 3NPI in slurry, w.r.t to solids (wt %) | 3.80 |
| NPI in slurry for experiment (wt %) | 22.00 |
| 3NPI in toluene, w.r.t to total 4NPI/3NPI, after 4 h stirring with bicarbonate (wt %) | 1.96 |
| 3NPI in toluene, w.r.t to total 4NPI/3NPI, after 8 h stirring with bicarbonate (wt %) | 1.56 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | NM |

Example 10

The purpose of this experiment was to show the efficiency of 3NPI removal from 4NPI at marginal mixing rate at higher temperature in, with more sodium bicarbonate in the process. The experiment was run exactly as in Example 1 except the NPI water slurry was contacted with bicarbonate at 50° C. at 68 rpm, in the presence of 4.0 wt % bicarbonate instead of 3 wt %. A sample of the bicarbonate treated slurry was contacted with toluene as in Example 1 and it was shown that 0.33 wt % of 3NPI remained in the 4NPI after 8 hours of contact time. More bicarbonate was efficient in removing the bulk of the 3NPI from the 4NPI, compared to Examples 3 and 4. The results are shown in Table 10.

TABLE 10

|  | Example# 10 |
|---|---|
| Stirring rate (rpm) | 68 |
| Temperature during experiment (° C.) | 50 |
| sodium bicarbonate w.r.t wt NPI in starting NPI slurry (wt %) | 4.0 |
| % NPI in slurry (wt %) | 25.40 |
| acid in slurry (wt %) | 0.10 |
| 3NPI in slurry, w.r.t to solids (wt %) | 3.50 |
| NPI in slurry for experiment (wt %) | 22.00 |
| 3NPI in toluene, w.r.t to total 4NPI/3NPI, after 4 h stirring with bicarbonate (wt %) | NM |
| 3NPI in toluene, w.r.t to total 4NPI/3NPI, after 8 h stirring with bicarbonate (wt %) | 0.33 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | NM |

Example 11 (Comparative)

The purpose of this experiment was to compare the performance of the process when sodium hydroxide was used instead of sodium bicarbonate.

The experiment was run exactly as in Example 1 except the NPI water slurry was contacted with sodium hydroxide at 50° C. at 68 rpm. The amount of bicarbonate typically employed was 3 wt % with respect to the weight of NPI. This represented 7.36 mole % sodium bicarbonate with respect to the moles of NPI present in the water slurry. The amount of sodium hydroxide used in this experiment was also 7.36 mole % with respect to the moles of NPI present in the water slurry. A sample of the treated slurry was contacted with toluene as in Example 1 and it was shown that 2.32 wt % of 3NPI remained in the 4NPI after 8 hours of contact time.

Our results showed that sodium hydroxide was highly ineffective and did not adequately selectively remove 3NPI from the 4NPI. The results are shown in Table 11.

TABLE 11

|  | Example# 11 |
|---|---|
| Stirring rate (rpm) | 68 |
| Temperature during experiment (° C.) | 50 |
| sodium bicarbonate w.r.t wt NPI in starting NPI slurry (wt %) | 1.43 NaOH instead of NaHCO3 |
| % NPI in slurry (wt %) | 24.80 |
| acid in slurry (wt %) | 0.07 |
| 3NPI in slurry, w.r.t to solids (wt %) | 3.50 |
| NPI in slurry for experiment (wt %) | 22.00 |
| 3NPI in toluene, w.r.t to total 4NPI/3NPI, after 4 h stirring with bicarbonate (wt %) | NM |
| 3NPI in toluene, w.r.t to total 4NPI/3NPI, after 8 h stirring with bicarbonate (wt %) | 2.32 |
| 3NPI in toluene, w.r.t to total 4NPI/3NPI, after 12 h stirring with bicarbonate (wt %) | NM |
| 3NPI in toluene, w.r.t to total 4NPI/3NPI, after 24 h stirring with bicarbonate (wt %) | NM |

1. NM means not measured.

The data in Tables 1-11 is shown in Table 12.

TABLE 12

|  | Example# | | | | | | | | | | |
|---|---|---|---|---|---|---|---|---|---|---|---|
|  | 1 | 2 | 3 | 4 | 5 | 6 | 7 | 8 | 9 | 10 | 11 |
| Stirring rate (rpm) | 68 | 500 | 500 | 68 | 68 | 110 | 68 | 68 | 68 | 68 | 68 |
| Temperature during experiment (° C.) | 31 | 41 | 31 | 41 | 50 | 50 | 60 | 20 | 55 | 50 | 50 |
| sodium bicarbonate w.r.t wt NPI in starting NPI slurry (wt %) | 3.0 | 3.0 | 3.0 | 3.0 | 3.0 | 3.0 | 3.0 | 3.0 | 1.8 | 4.0 | 1.43 NaOH instead of NaHCO3 |
| % NPI in slurry (wt %) | 24.50 | 24.50 | 24.50 | 24.50 | 24.50 | 24.50 | 27.04 | 27.04 | 27.00 | 25.40 | 24.80 |
| acid in slurry (wt %) | 0.10 | 0.10 | 0.10 | 0.10 | 0.10 | 0.10 | 0.07 | 0.07 | 0.07 | 0.10 | 0.07 |
| 3NPI in slurry, w.r.t to solids (wt %) | 3.54 | 3.54 | 3.54 | 3.54 | 3.54 | 3.54 | 3.66 | 3.66 | 3.80 | 3.50 | 3.50 |
| NPI in slurry for experiment (wt %) | 22.5 | 22.0 | 22.0 | 22.0 | 22.0 | 22.0 | 22.0 | 22.0 | 22.00 | 22.00 | 22.00 |

TABLE 12-continued

| | Example# | | | | | | | | | | |
|---|---|---|---|---|---|---|---|---|---|---|---|
| | 1 | 2 | 3 | 4 | 5 | 6 | 7 | 8 | 9 | 10 | 11 |
| 3NPI in toluene, w.r.t to total 4NPI/3NPI, after 4 h stirring with bicarbonate (wt %) | NM | NM | NM | 2.26 | NM | NM | 0.58 | 3.07 | 1.96 | NM | NM |
| 3NPI in toluene, w.r.t to total 4NPI/3NPI, after 8 h stirring with bicarbonate (wt %) | 2.47 | 0.35 | 1.78 | 1.80 | 0.57 | 0.85 | 0.49 | 3.02 | 1.56 | 0.33 | 2.32 |
| 3NPI in toluene, w.r.t to total 4NPI/3NPI, after 12 h stirring with bicarbonate (wt %) | NM | NM | NM | 1.27 | NM | NM | NM | NM | NM | NM | NM |
| 3NPI in toluene, w.r.t to total 4NPI/3NPI, after 24 h stirring with bicarbonate (wt %) | 1.61 | 0.32 | 0.59 | 0.34 | 0.44 | 0.31 | NM | NM | NM | NM | NM |

1. NM means not measured.

Example 12

Conversion of Treated 4NPI to Bisimide

A 2-liter, 5-necked oil jacketed glass vessel, equipped with a Dean and Stark receiver topped with a reflux condenser, a mechanical stirrer, and means for maintaining a nitrogen atmosphere, was charged with 335 g (1.63 mol) of 4-NPI in 1000 g of toluene (resulting from the bicarbonate treatment of the 4NPI/water slurry, see above), and 6.2 g (0.008 mol HEG-Cl) of a catalyst solution composed of 34.4% by wt. HEG-Cl, 10.0% sodium chloride, and 55.6% water. An additional 500 g of toluene was added. The solution was brought to reflux using an external hot oil unit set at 120° C. to supply hot oil to the jacket of the vessel, and the water was removed by azeotropic distillation. Approximately 500 g of toluene was removed during the distillation. The dry 4-NPI/catalyst toluene solution was then added via a flexible fitting to a 5-liter, 5-necked oil jacketed glass vessel (equipped with a Dean and Stark Receiver topped with a reflux condenser, mechanical stirrer, and means for maintaining a nitrogen atmosphere) containing 222 g (8.15 mol) of BPA disodium salt and 700 g of toluene (the salt solution can also be added to the NPI solution). The temperature on the 5-liter vessel was maintained at 120° C. using a hot oil recirculating unit. HPLC of the reaction mixture indicated that the displacement reaction was complete in 60 min. to afford a 99.4% yield of BPA bisimide. The mixture was cooled to 80° C. and extractively purified with three 580 mL portions of 1% aqueous sodium hydroxide to afford pure bisimide with a yellowness index (YI) of 2.0.

The YI was measured with a Macbeth 7000 spectrometer using ASTM D-1925. A blank of methylene chloride was measured for YI prior to measurement of the sample. This $YI_{blank}$ measurement was recorded for use in correcting the final measurement. About 0.5 g of a sample was dissolved into 10 mL of methylene chloride. The sample was then filtered through a 0.5 g HPLC filter. The mixture was then transferred to a 3.7 cm×5 cm×10 mm path length cell. The cell was placed into the calorimeter (ASTM D11925) and the YI was determined.

The equation (I) below was used to correct the YI. This equation (I) is general and allows for solutions to also be measured for YI.

$$YI_{cor} = (YI_{meas} - YI_{blank}) * 0.5 * 100 / (\text{wt. Sample in } G * \% \text{ solids of the sample}) \quad (I)$$

The washes were done at 80° C., with a 5 minute agitation time and a 7 minute settling time. The YI of the material was 2.2. The YI of a typical reaction (without bicarbonate treatment of the 4NPI/water slurry) is 3 to 4.

Example 13

A 10,570 gallon steam jacketed vessel was charged with 9427 pounds of 4-NPI and 25500 pounds of toluene under an atmosphere of nitrogen. The material resulted from the bicarbonate treatment of the 4NPI/water slurry described above. Approximately 9000 more pounds of toluene was added to the vessel. The content of the vessel was at ~115° C. The mixture was agitated with a mechanical stirrer and 18 gallons of a brine solution of HEG-Cl (28.6% by wt. HEG-Cl, ~10% sodium chloride, 46# of HEG-Cl) was added over a period of 10 minutes. The water was allowed to azeotrope out of the vessel through a reflux condenser. The temperature of the mixture was ~110° C. upon completion of the catalyst addition. Steam was applied to the jacket and ~9000 pounds of toluene was removed via distillation, at which point the temperature of the mixture was ~119° C. Approximately 6200 pounds of BPA salt in ~17000# of toluene was added to the vessel. The ensuing exothermic reaction resulted in a 3 degree temperature rise. 4-NPI/toluene can be added to the reaction mixture to adjust the stoichiometry of 4-NPI to BPA salt.

The reaction mixture was cooled to 80° and extractively purified with two 840 gallons portions of 1% aqueous sodium hydroxide, and one 500 gallon portion of water to afford pure bisimide. The washes were done at 80° C., with a 5 minute agitation time and a 7 minute settling time. The YI of the material was 2.2. The YI of a typical reaction (without bicarbonate treatment of the 4NPI/water slurry) is 3 to 4.

Example 14

Isolation of Purified Bisimide

The toluene was removed from the bisimide at 250 to 300° C. under reduced pressure (50 mm to 300 mm) in a continuous manner in process equipment known in the art to afford molten bisimide. The residence time of the bisimide in the devolitilizing equipment was on the order of 30 seconds to 1 hour.

Example 15

Conversion of Purified Bisimide to BPADA

Bisimide was continuously feed to a stirred reactor maintained at 180° C. at 210 psig along with water containing dissolved phthalic acid and triethylamine, and additional molten phthalic anhydride. The ratio of bisimide:water:phthalic-acid:triethylamine:phthalic-anhydride was 2.7 to 10.8 to 2.7 to 3.0 to 1.0. These ratios can be adjusted as desired. The material had a residence time in the reactor of 60 minutes to afford an equilibrium mixture of bisimide, N-methylphthalimide, phthalic acid-triethylamine salts, BPA-tetraacid-triethylamine salts, BPA-triacid-N-methylamide-triethylamine salts dissolved in water.

The reaction mixture is then continuously fed to an extraction column were it is continuously contacted with toluene containing 3.0 to 10.0 wt % triethylamine at ~170° C. at ~170 psig to remove unreacted bisimide and N-methylphthalimide. The toluene phase exits the column from the top. The extracted aqueous phase exits the column from the bottom and contains BPA-tetraacid-triethylamine salts, BPA-triacid-N-methylamide-triethylamine salts, and phthalic acid-triethylamine salts dissolved in water. The mixture is then continuously fed to equipment at sufficient temperatures and pressures to remove the water, triethylamine, and phthalic acid (as phthalic anhydride) as a vapor stream to afford molten BPADA. The temperatures must be maintained to remove the water, triethylamine, and phthalic acid but not to impact the final color of the BPADA product.

The yellowness index (YI) of the BPADA resulting from the initial use of bicarbonate treated 4NPI was measured in accordance to Example 12 and was 4 to 6, as compared to a YI 6 to 9 when bicarbonate treatment was not practiced.

Example 16

Synthesis of Polymer from BPADA Resulting from the Initial Use of Bicarbonate Treated 4-NPI The molten BPADA from Example 4 was dissolved in a suitable solvent (in the case orthodichlorobenzene) at a suitable temperature (100 to 180° C.) at a suitable concentration (5 to 60 wt %). The BPADA solution (1500# of BPADA and 2800# of ODCB) was then charged to a reactor and heated to 150° C. A chain terminating reagent was added (phthalic anhydride, 17#). Meta-phenylene diamine (313#) was metered into the reactor. The reaction mixture was heated to 180° C. for one hour and a sample was taken to determine the molecular weight and the stoichiometry (monomer ratio) of the resin (see U.S. Pat. No. 7,041,773). The polymer solution was then conveyed to hold vessel. The material in the hold vessel was continuously fed to a wiped film evaporator operated at a temperature and pressure necessary to remove all the solvent and afford molten polymer that is pumped through a die-face to form a strand that is pulled through a water bath (for cooling), a dryer (to remove water), and a chopper to afford polymer pellets with a YI of <60. The yellowness index (YI) of the polymer resulting from the initial use of bicarbonate treated 4NPI was 58 to 61, as compared to a polymer YI 65 to 75 when bicarbonate treatment is not practiced.

The YI was measured with a Macbeth 7000 spectrometer using ASTM D-1925. A polymer plaque having the dimensions of 3"×2"×0.125" (7.6 cm.×5.1 cm×0.32 cm) was molded from the polymer. The YI of the plaque was measured with the Macbeth 7000 spectrometer using ASTM D-1925.

In describing the embodiments of the present invention, specific terminology is employed for the sake of clarity. The invention, however, is not intended to be limited to the specific terminology so selected, and it is to be understood that each specific element includes all technical equivalents that operate in a similar manner to accomplish similar functions. Having thus described exemplary embodiments of the present invention, it should be noted by those skilled in the art that the within disclosures are exemplary only, and that various other alternatives, adaptations, and modifications may be made within the scope of the present invention. Accordingly, the present invention is not limited to the specific embodiments illustrated herein, but is limited only by the following claims.

We claim:

1. A process for isolating 4-nitro-N-alkylphthalimide from an aqueous mixture of 4-nitro-N-alkylphthalimide and 3-nitro-N-alkylphthalimide comprising the steps of:
   (a) providing a first mixture comprising (i) solids comprising 4-nitro-N-alkylphthalimide and 3-nitro-N-alkylphthalimide and (ii) water;
   (b) adding a salt selected from the group consisting of alkali metal carbonates, alkali metal hydrogen carbonates, alkaline earth metal carbonates, hydrogen carbonates and mixtures thereof to the first mixture, thereby forming a second mixture;
   (c) stirring the second mixture under conditions sufficient for selective hydrolysis of the imide linkage of 3-nitro-N-alkylphthalimide into a water-soluble acid-amide salt of 3-nitro-N-alkylphthalimide, thereby forming a third mixture;
   (d) adding an organic solvent to the third mixture, thereby forming a fourth mixture comprising (i) an organic phase comprising 4-nitro-N-alkylphthalimide dissolved in the organic solvent and (ii) an aqueous phase comprising dissolved acid-amide salt of 3-nitro-N-alkylphthalimide; and
   (e) separating the organic phase from the aqueous phase.

2. The process of claim 1, wherein in step (a), the first mixture is elevated to a temperature ranging from 20 to 60° C.

3. The process of claim 1, wherein in step (a) through step (c), the first mixture and second mixture are maintained at a temperature ranging from 20 to 60° C.

4. The process of claim 1, wherein in step (a), the first mixture is provided comprising from 10 to 40 weight percent solids and from 90 to 60 weight percent water.

5. The process of claim 1, wherein in step (a), the first mixture is provided comprising from 20 to 30 weight percent solids and from 80 to 70 weight percent water.

6. The process of claim 1, wherein in step (a), the first mixture is provided further comprising proton-bearing impurities; in step (c), the proton bearing impurities are converted to water soluble alkali metal salts; and in step (d) the aqueous phase further comprises dissolved alkali metal salts of the proton-bearing impurities.

7. The process of claim 6, wherein in step (a), the proton-bearing impurities are selected from the group consisting of residual nitric acids, sulfuric acids, nitrophthalic acids, oxalic acids, and combinations thereof.

8. The process of claim 6, wherein in step (a), the solids comprise from 94.0 to 99.9 weight percent 4-nitro-N-alkylphthalimide, from 0.1 to 5.0 weight percent 3-nitro-N-alkylphthalimide, and from more than 0 to 1.0 weight percent proton-bearing impurities.

9. The process of claim 1, wherein in step (b), the salt is sodium carbonate or sodium hydrogen carbonate.

10. The process of claim 1, wherein in step (b), the salt is added in an amount ranging from 0.1 to 7 weight percent of salt, based on the total weight percent of solids in the first mixture.

11. The process of claim 1, wherein in step (b), the salt is added in an amount ranging from 1 to 5 weight percent of salt, based on the total weight percent of solids in the first mixture.

12. The process of claim 1, wherein in step (c), the second mixture is stirred for a period ranging from 2 to 48 hours.

13. The process of claim 1, wherein in step (c), the second mixture is stirred for a period ranging from 2 to 8 hours.

14. The process of claim 1, wherein in step (c), the second mixture is stirred for a period ranging from 2 to 4 hours.

15. The process of claim 1, wherein in step (c), the third mixture has a pH ranging from 8.5 to 12.

16. The process of claim 1, wherein in step (d), the organic solvent is selected from the group consisting of toluene, xylene, chlorobenzene benzene, and combinations thereof.

17. The process of claim 16, wherein in step (d) the organic solvent is toluene.

18. The process of claim 6, wherein in step (d), the organic phase comprises from more than 0 to less than 2 weight percent 3-nitro-N-alkylphthalimide and proton-bearing impurities, based on the total weight percent of 3-nitro-N-alkylphthalimide, 4-nitro-N-alkylphthalimide and proton-bearing impurities.

19. The process of claim 6, wherein in step (d), the organic phase comprises from more than 0 to less than 1 weight percent 3-nitro-N-alkylphthalimide and more than 0 to less 500 parts per million proton-bearing impurities, based on the total weight percent of 3-nitro-N-alkylphthalimide, 4-nitro-N-alkylphthalimide and proton-bearing impurities.

20. The process of claim 1, prior to step (a), further comprising the steps of nitrating N-alkylphthalimide in an acid selected from the group consisting of nitric acid and mixtures of nitric acid and sulfuric acid to form a nitration product, and washing with water the nitration product to form the first mixture.

21. The process of claim 1, wherein in step (a), the first mixture further comprises a member selected from the group consisting of 4-substituted-nitro-N-alkylphthalimide, 3-substituted-nitro-N-alkylphthalimide, and mixtures thereof; wherein substituted substituents are selected from the group consisting of chloro substituents, bromo substituents, fluoro substituents, and combinations thereof.

22. A process for isolating 4-nitro-N-alkylphthalimide from an aqueous mixture of 4-nitro-N-alkylphthalimide, 3-nitro-N-alkylphthalimide, and proton-bearing impurities comprising the steps of:
   (a) providing a first mixture comprising a water slurry comprising solids comprising 4-nitro-N-alkylphthalimide, 3-nitro-N-alkylphthalimide, and proton-bearing impurities;
   (b) adding a salt selected from the group consisting of sodium carbonate and sodium hydrogen carbonate to the first mixture, thereby forming a second mixture;
   (c) stirring the second mixture under conditions sufficient for selective hydrolysis of the imide linkage of 3-nitro-N-alkylphthalimide into a water-soluble acid-amide salt of 3-nitro-N-alkylphthalimide and to convert the proton-bearing impurities to water soluble alkali metal salts, thereby forming a third mixture;
   (d) adding toluene to the third mixture, thereby forming a fourth mixture comprising (i) an organic phase comprising 4-nitro-N-alkylphthalimide dissolved in toluene and (ii) an aqueous phase comprising dissolved acid-amide salt of 3-nitro-N-alkylphthalimide and alkali metal salts of the proton-bearing impurities; and
   (e) separating the organic phase from the aqueous phase.

23. The process of claim 22, wherein in step (a), the first mixture is elevated to a temperature ranging from 20 to 60° C.

24. The process of claim 22, wherein in step (a) through step (c), the first mixture and second mixture are maintained at a temperature ranging from 20 to 60° C.

25. The process of claim 22, wherein in step (a), the proton-bearing impurities are selected from the group consisting of residual nitric acids, sulfuric acids, nitrophthalic acids, oxalic acids, and combinations thereof.

26. The process of claim 22 wherein in step (a), the solids comprise from 94.0 to 99.9 weight percent 4-nitro-N-alkylphthalimide, from 0.1 to 5.0 weight percent 3-nitro-N-alkylphthalimide, and from more than 0 to 1.0 weight percent proton-bearing impurities.

27. The process of claim 22, wherein in step (a), the first mixture is provided comprising from 20 to 30 weight percent solids and from 80 to 70 weight percent water.

28. The process of claim 22, wherein in step (b), the salt is added in an amount ranging from 1 to 5 weight percent of salt, based on the total weight percent of solids in the first mixture.

29. The process of claim 22, wherein in step (c), the second mixture is stirred for a period ranging from 2 to 48 hours.

30. The process of claim 22 wherein in step (c), the third mixture has a pH ranging from 8.5 to 12.

31. The process of claim 22, wherein in step (d), the organic phase comprises from more than 0 to less than 2 weight percent 3-nitro-N-alkylphthalimide and proton-bearing impurities, based on the total weight percent of 3-nitro-N-alkylphthalimide, 4-nitro-N-alkylphthalimide and proton-bearing impurities.

32. The process of claim 22, wherein in step (d), the organic phase comprises from more than 0 to less than 1 weight percent 3-nitro-N-alkylphthalimide and more than 0 to less 500 parts per million proton-bearing impurities, based on the total weight percent of 3-nitro-N-alkylphthalimide, 4-nitro-N-alkylphthalimide and proton-bearing impurities.

* * * * *